United States Patent [19]

Ohsawa et al.

[11] Patent Number: 5,444,375
[45] Date of Patent: Aug. 22, 1995

[54] IONIZATION CURRENT DETECTOR FOR DETECTING THE IONIZATION CURRENT GENERATED IN A PLURALITY OF IGNITION COILS OF AN INTERNAL COMBUSTION ENGINE

[75] Inventors: Toshio Ohsawa; Shigemi Murata, both of Hyogo, Japan

[73] Assignee: Mitsubishi Denki Kabushiki Kaisha, Tokyo, Japan

[21] Appl. No.: 978,719

[22] Filed: Nov. 19, 1992

[30] Foreign Application Priority Data

Nov. 26, 1991 [JP] Japan .................................. 3-310715

[51] Int. Cl.6 .............................................. F02P 17/12
[52] U.S. Cl. ...................................... 324/380; 324/399; 324/402
[58] Field of Search ............... 324/380, 383, 393, 399, 324/402; 73/116

[56] References Cited

U.S. PATENT DOCUMENTS 4,762,106  8/1988  Blauhut .
5,067,462  11/1991 Iwata et al. .
5,269,282  12/1993 Miyata et al. .................. 324/399 X

FOREIGN PATENT DOCUMENTS 2802196  7/1979  Germany .

Primary Examiner—Sandra L. O'Shea
Assistant Examiner—Warren S. Edmonds
Attorney, Agent, or Firm—Sughrue, Mion, Zinn, Macpeak & Seas; Richard C. Turner; Marie-Claire Boisvert

[57] ABSTRACT

An ionization current detector for an internal combustion engine which includes a single ionization current detecting circuit 11 connected to a plurality of ignition coils 1 for detecting an ionization current flowing through at least one of the ignition coils 1 upon combustion of the fuel. Accordingly, an ionization current detector which is simple in organization and inexpensive can be obtained.

2 Claims, 3 Drawing Sheets

IONIZATION CURRENT DETECTOR FOR DETECTING THE IONIZATION CURRENT GENERATED IN A PLURALITY OF IGNITION COILS OF AN INTERNAL COMBUSTION ENGINE

BACKGROUND OF THE INVENTION

This invention relates to ionization current detectors for internal combustion engines having a plurality of ignition coils and detecting ionization current flowing through the ignition coils during combustion of a mixed gas.

FIG. 3 shows a circuit diagram of a conventional detector, in which reference numeral 1 designates an ignition coil having a primary side 1a and a secondary side 1b and arranged on each of cylinders of an internal combustion engine; 2, a power transistor connected to the primary side 1a for cutting off the primary current; 3, a spark plug connected to the secondary side 1b for firing a mixed gas of a not shown internal combustion engine by applying a high ignition voltage; 4, a capacitor connected to the positive pole of the secondary side 1b; 5, a resistor inserted between the capacitor 4 and a ground for converting ionization current to a voltage; and 6, a diode connected to the resistor 5 in parallel therewith.

Reference numeral 7 designates a Zener diode inserted between the secondary side 1b and a coil power supply 10; 8, an AC coupler circuit for extracting only an AC component out of the voltage obtained at the resistor 5; 9, a comparator circuit for comparing the voltage obtained at the AC coupler circuit 9 with a predetermined reference level; 11, an ionization current detector circuit consisting of the components designated by reference numerals 4 through 9. As many power transistors 2 and ionization current detector circuits 11 as ignition coils 1 are provided. Reference numeral 12 designates an OR circuit for receiving outputs of the respective ionization current detector circuits 11 and ORing these outputs; and 13, an output terminal for outputting a combustion pulse from the OR circuit 12 when the ionization current has been detected.

In the above organization, when each power transistor 2 turns off at an ignition timing of the internal combustion engine and the primary current flowing through the primary side 1a is then cut off, a negative high ignition voltage is generated at the secondary side 1b. As a result, a spark occurs across the electrodes of each spark plug 3, firing the mixed gas in the internal combustion engine. At this point, ionization takes place in association with combustion of the mixed gas, producing ions.

Here, the electrodes of each spark plug 3 act as electrodes for detecting the ionization current after the spark. The ionization current flows by the movement of electrons caused by the positively biased voltage of the capacitor 4. The generation of the ionization current in turn generates a voltage across each resistor 5. The AC component of this voltage is extracted by each AC coupler circuit 8, and the extracted AC component is compared with the reference level at each comparator circuit 9, whereby a combustion pulse is generated from each comparator circuit 9. The combustion pulses from these comparator circuit 9 are ORed at the OR circuit 12, producing a combustion pulse from the output terminal 13. Combustion of the mixed gas is verified by detection of such combustion pulse.

The thus organized conventional detector requires that as many ionization current detector circuit 11 as ignition coils be provided, which has made the organization complicated and expensive.

SUMMARY OF THE INVENTION

It is therefore an object of the invention to overcome the above problem and provide a simply organized, inexpensive ionization current detector for an internal combustion engine.

The above object is accomplished according to the principle of this invention by an ionization current detector for an internal combustion engine, which comprises an ionization current detecting means connected to a plurality of ignition coils for detecting an ionization current flowing through each of the ignition coils while the mixed gas is being burnt.

The ionization current detecting means which detects the ionization current flowing through the ignition coil is connected to a plurality of ignition coils. A single ionization current detecting means can detect the ionization current of the plurality of ignition coils, thus contributing to reducing the number of ionization current detecting means.

The novel features which are believed to be characteristic of this invention are set forth with particularity in the appended claims.

DETAILED DESCRIPTION OF THE PREFERRED EMBODIMENTS

This invention itself may best be understood from the detailed description of the preferred embodiments taken in connection with the accompanying drawings. Embodiments of this invention will be described with reference to the accompanying drawings.

(Embodiment 1)

Figure 1:
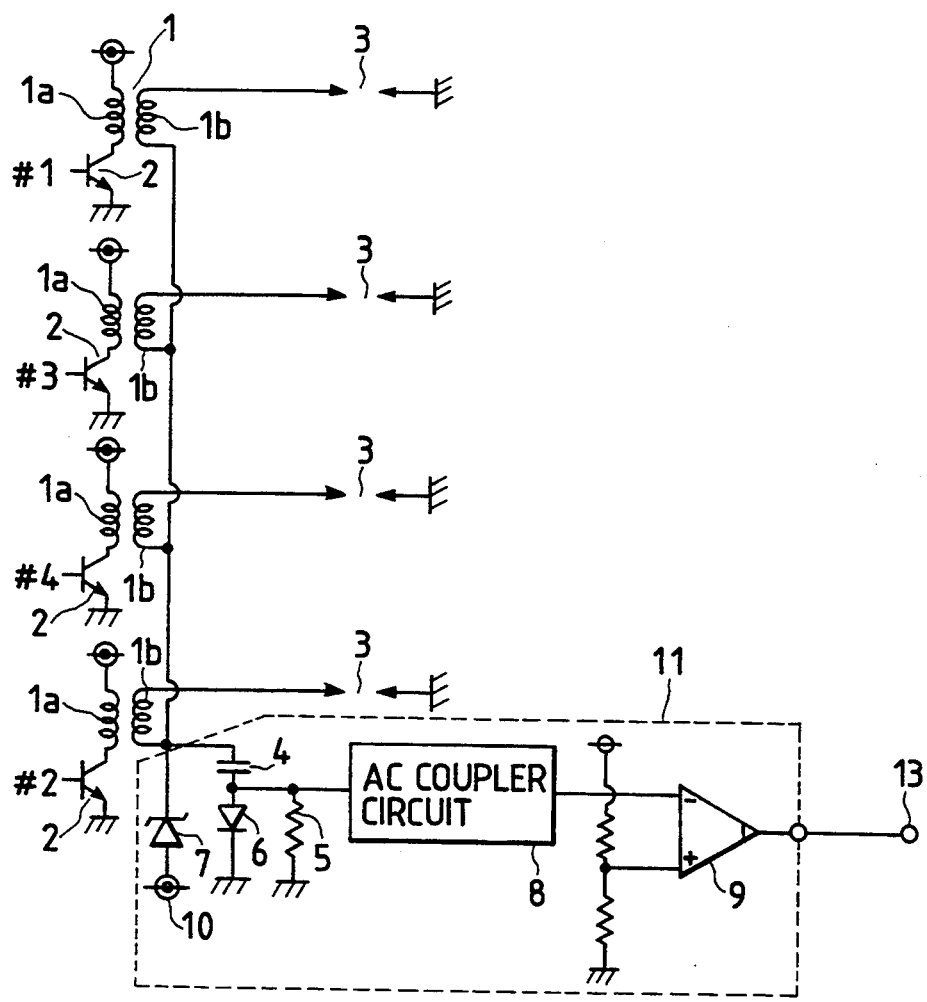
FIG. 1 is a diagram showing the organization of an ionization current detector for an internal combustion engine, which is a first embodiment of this invention.

FIG. 1 shows the organization of an ionization current detector, which is a first embodiment of this invention. While an ionization current detector circuit 11 is the same as the conventional one, only a single circuit is used to be connected to ignition coils 1 respectively provided for the cylinders. Therefore, the ionization current flowing through each ignition coil 1 during combustion of the mixed gas is converted to voltage by a resistor 5, and the voltage is then fed to an AC coupler circuit 8 at the subsequent stage (thus synthesized). The AC component of this voltage is extracted at the AC coupler circuit 8, and the AC component is then compared with a predetermined reference level at a comparator circuit 9. Combustion of the mixed gas in each cylinder is verified by a combustion pulse outputted from the comparator circuit 9.

(Embodiment 2)

Figure 2:
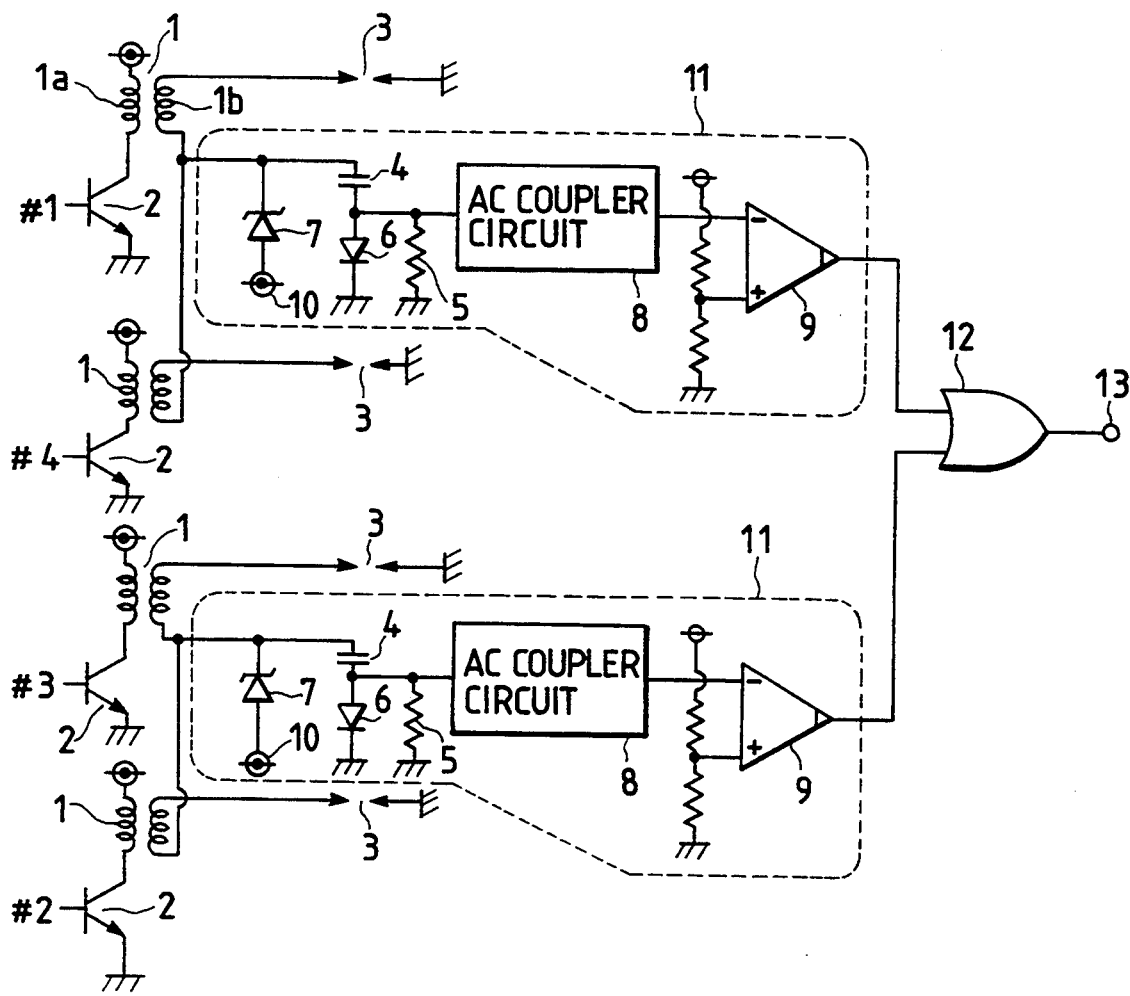
FIG. 2 is a diagram showing the organization of an ionization current detector for an internal combustion engine, which is a second embodiment of this invention.
Figure 3:
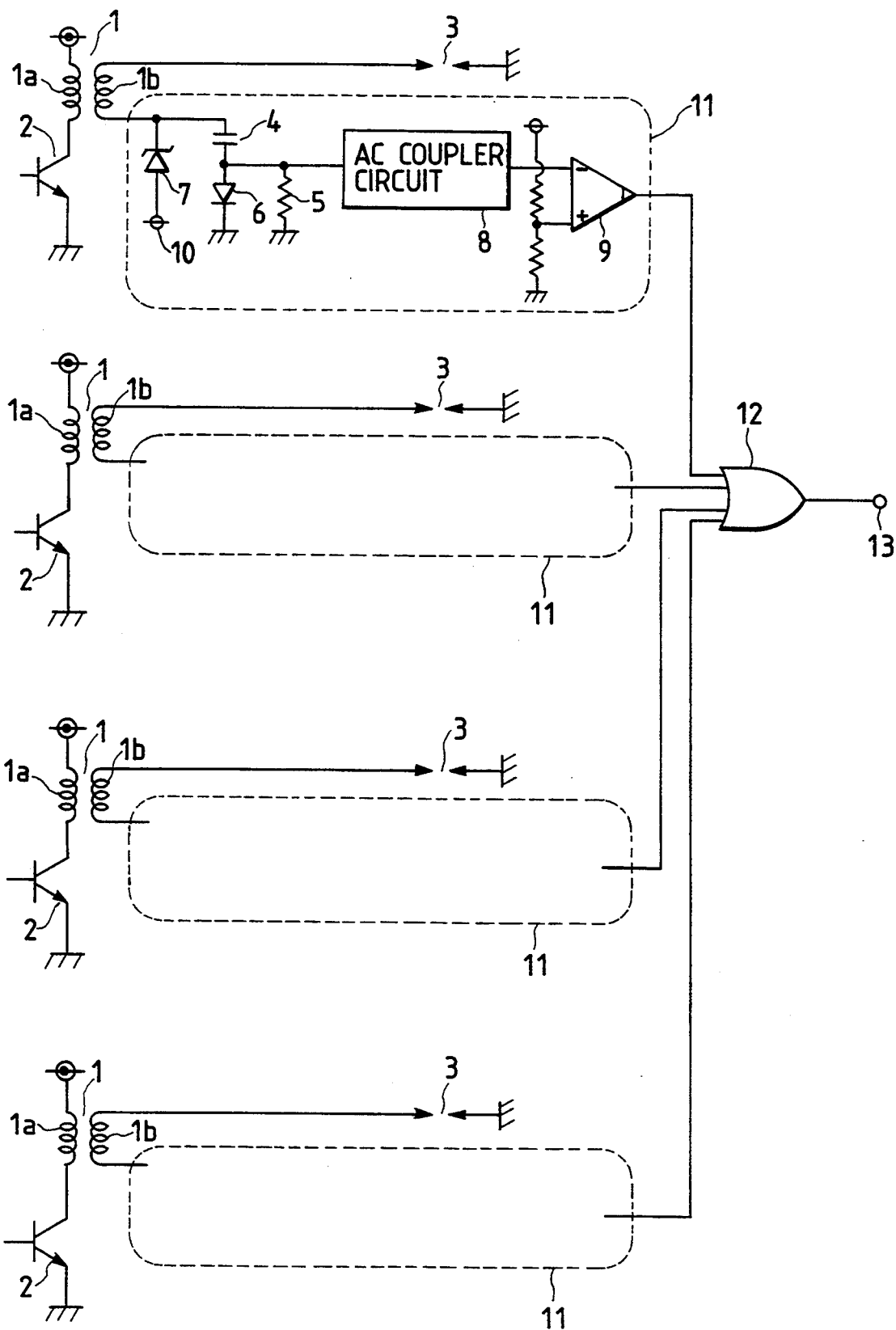
FIG. 3 is a diagram showing the organization of a conventional ionization current detector.

FIG. 2 shows the organization of an ionization current detector, which is a second embodiment of this invention. A single ionization current detecting circuit 11 is connected to the ignition coils to be ignited every other ignition timing, i.e., a pair of ignition coils (e.g., ignition coils Nos. 1 and 4 or ignition coils Nos. 2 and 3 in FIG. 2). Thus, the outputs of the two ionization current detector circuit 11 are applied to the OR circuit 12, such that a combustion pulse is outputted from the output terminal 13 of the OR circuit 12.

While the organization in which the ionization current is converted to voltage by the resistor 5 has been proposed in the respective embodiments, other organizations may of course be applied.

As described above, this invention is characterized as connecting the ionization current detecting means to a plurality of ignition coils and detecting combustion of the mixed gas in each of the cylinders from the ionization current flowing through each of the ignition coils. Therefore, the ionization current detector of this invention can achieve a simple organization at a low cost and ensure reliability even when applied to high-speed, multi-cylinder engines.

While description has been made of the particular embodiments of this invention, it will be understood that many modifications may be made without departing from the spirit thereof. The appended claim is contemplated to cover any such modifications as fall within the true spirit and scope of this invention.

What is claimed is:

1. An ionization current detector for an internal combustion engine, comprising:

ignition coils for generating a high ignition voltage;

ignition plugs respectively provided on a plurality of cylinders for firing mixed gas by a spark upon application of said high ignition voltage, wherein ionization currents are generated when said ignition plugs are fired, respectively; and a single ionization current detecting means, coupled to said ignition coils, for detecting said ionization currents flowing through said ignition coils during combustion of said mixed gas; wherein said single ionization current detecting means detects said ionization currents by synthesizing said ionization currents flowing through said ignition coils.

2. An ionization current detector for an internal combustion engine, comprising:

at least one pair of ignition coils for generating a high ignition voltage;

ignition plugs respectively provided on a plurality of cylinders for firing mixed gas by a spark upon application of said high ignition voltage, wherein ionization currents are generated when said ignition plugs are fired, respectively; and an ionization current detecting means for detecting ionization currents flowing through said ignition coils during combustion of said mixed gas; wherein said ionization current detecting means detects said ionization currents by synthesizing said ionization currents flowing through said ignition coils, wherein said ionization current detecting means are connected to each pair of said ignition coils.

* * * * *